United States Patent
Yue et al.

(10) Patent No.: US 6,962,799 B2
(45) Date of Patent: Nov. 8, 2005

(54) MICROTUBULE-ASSOCIATED PROTEINS AND TUBULINS

(75) Inventors: Henry Yue, Sunnyvale, CA (US); Danniel B. Nguyen, San Jose, CA (US); Catherine M. Tribouley, San Francisco, CA (US); Olga Bandman, Mountain View, CA (US); Y. Tom Tang, San Jose, CA (US); Preeti G. Lal, Santa Clara, CA (US); Narinder K. Chawla, Union City, CA (US); Jennifer L. Policky, San Jose, CA (US)

(73) Assignee: Incyte Corporation, Wilmington, DE (US)

( * ) Notice: Subject to any disclaimer, the term of this patent is extended or adjusted under 35 U.S.C. 154(b) by 133 days.

(21) Appl. No.: 10/362,247

(22) PCT Filed: Aug. 20, 2001

(86) PCT No.: PCT/US01/25987

§ 371 (c)(1),
(2), (4) Date: Feb. 19, 2003

(87) PCT Pub. No.: WO02/16587

PCT Pub. Date: Feb. 28, 2002

(65) Prior Publication Data

US 2004/0077837 A1 Apr. 22, 2004

Related U.S. Application Data

(60) Provisional application No. 60/236,015, filed on Sep. 27, 2000, and provisional application No. 60/226,797, filed on Aug. 21, 2000.

(51) Int. Cl.$^7$ .......................... C12P 21/02; C07H 21/04
(52) U.S. Cl. .............. 435/69.1; 435/252.3; 435/254.11; 435/325; 536/23.5
(58) Field of Search .............................. 435/69.1, 252.3, 435/254.11, 325; 536/23.5

(56) References Cited

U.S. PATENT DOCUMENTS

2003/0073623 A1 * 4/2003 Drmanac et al. ............. 514/12
2003/0152926 A1 * 8/2003 Murray et al. ................. 435/6

FOREIGN PATENT DOCUMENTS

WO    WO 01/54472 A2 * 8/2001
WO    WO 01/55163 A1 * 8/2001

\* cited by examiner

*Primary Examiner*—Robert A. Wax
(74) *Attorney, Agent, or Firm*—Foley & Lardner LLP

(57) ABSTRACT

The invention provides human microtubule-associated proteins and tubulins (MICAPTUB) and polynucleotides which identify and encode MICAPTUB. The invention also provides expression vectors, host cells, antibodies, agonists, and antagonists. The invention also provides methods for diagnosing, treating, or preventing disorders associated with aberrant expression of MICAPTUB.

15 Claims, No Drawings

MICROTUBULE-ASSOCIATED PROTEINS AND TUBULINS

TECHNICAL FIELD

This invention relates to nucleic acid and amino acid sequences of microtubule-associated proteins and tubulins and to the use of these sequences in the diagnosis, treatment, and prevention of cell proliferative, autoimmune/inflammatory, vesicle trafficking, neurological, cell motility, reproductive, and muscle disorders, and in the assessment of the effects of exogenous compounds on the expression of nucleic acid and amino acid sequences of microtubule-associated proteins and tubulins.

BACKGROUND OF THE INVENTION

The cytoskeleton, a cytoplasmic system of protein fibers, mediates cell shape, structure, and movement. The cytoskeleton supports the cell membrane and forms tracks along which organelles and other elements move in the cytosol. The cytoskeleton is a dynamic structure that allows cells to adopt various shapes and to carry out directed movements. Major cytoskeletal fibers are the microfilaments, the microtubules, and the intermediate filaments. Motor proteins including myosin, dynein, and kinesin, drive movement of or along the fibers. Accessory or associated proteins modify the structure or stability of the fibers while cytoskeletal membrane anchors connect the fibers to the cell membrane.

Microtubules, cytoskeletal fibers with a diameter of 24 nm, have multiple roles in the cell. Bundles of microtubules form cilia and flagella, which are whip-like extensions of the cell membrane that are necessary for sweeping materials across an epithelium and for swimming of sperm, respectively. Marginal bands of microtubules in red blood cells and platelets are important for these cells' pliability. Organelles, membrane vesicles, and proteins are transported throughout the cell by motor proteins running along tracks of microtubules. For example, microtubules run through nerve cell axons, allowing bi-directional transport of materials and membrane vesicles between the cell body and the nerve terminal. Failure to supply the nerve terminal with these vesicles blocks the transmission of neural signals. During cell migration, differentiation, and the cell cycle, the microtubule cytoskeleton must rapidly reorganize through assembly and disassembly. Microtubules, in the form of the spindle, are also critical to chromosomal movement during cell division. Both stable and short-lived populations of microtubules exist in the cell.

Microtubules are a polymer of GTP-binding tubulin protein subunits. Each subunit is a heterodimer of $\alpha$- and $\beta$-tubulin, multiple isoforms of which exist. Tubulin binds two molecules of GTP at two different sites, and all three tubulins share an invariant glycine rich region thought to be involved in controlling access to one of the nucleotide binding sites (PROSITE PDOC00199). The tubulins share a motif with FtsZ, a polymer-forming GTPase necessary for bacterial cell division (PROSITE PDOC00873). Alpha-tubulin undergoes a number of post-translational modifications, including acetylation, polyglutamylation, truncation of two amino acids (forming $\Delta 2$ tubulin), and tyrosination. In some cases, these modifications can affect microtubule stability. In addition, $\beta$-tubulin auto-regulates the stability of its own mRNA. Free $\beta$-tubulin binds a conserved motif at the N-terminus of a nascent beta-tubulin chain. This activates an RNAse which degrades the polysome-bound mRNA (PROSITE PDOC00200). The hydrolysis of GTP is linked to the addition of tubulin subunits at the end of a microtubule. The subunits interact head to tail to form protofilaments; the protofilaments interact side to side to form a microtubule. A microtubule is polarized, one end ringed with $\alpha$-tubulin and the other with $\beta$-tubulin, and the two ends differ in their rates of assembly. Microtubules constantly "treadmill," exchanging their subunits with pools of free tubulin in the cytoplasm. This flow of subunits from one end of the microtubule to the other is created by differences in the critical subunit concentrations at opposite ends of the microtubule and is responsible for the dynamics of microtubule arrays (Margolis, R. L. and L. Wilson (1998) Bioessays 20:830–836). Each microtubule is generally composed of 13 protofilaments although 11 or 15 protofilament-microtubules are sometimes found. Cilia and flagella contain doublet microtubules. Microtubules grow from specialized structures known as centrosomes or microtubule-organizing centers (MTOCs). MTOCs may contain one or two centrioles, which are pinwheel arrays of triplet microtubules. The basal body, the organizing center located at the base of a cilium or flagellum, contains one centriole. $\gamma$-tubulin present in the MTOC is important for nucleating the polymerization of $\alpha$- and $\beta$-tubulin heterodimers but does not polymerize into microtubules.

Altered microtubule structure are correlated with numerous neuropathologies, including Alzheimer's disease (Terry, R. D. (1998) J. Neural Transm. Suppl. 53:141–145). An extraskeletal myxoid chondrosarcoma tumor from human contained parallel arrays of microtubules within the rough endoplasmic reticulum (Suzuki, T. et al. (1988) J. Pathol. 156:51–57). Microtubular aggregates were also found in hepatocytes from chimpanzees infected with hepatitis C virus. Altered mictrotubule structures are proposed to have a role in lens opacification (Clark, J. I. et al. (1999) Eye 13:417–424). Microtubules are also a proven target for anti-tumor drugs (Davis, A. et al. (1999) Neoplasia 1:498–507; for a review, see Jordan, A. et al. (1998) Med. Res. Rev. 18:259–296).

Microtubule-associated proteins (MAPs) have roles in the assembly and stabilization of microtubules, one of the major cytoskeletal fibers. A major family of MAPs, assembly MAPs, can be identified in neurons as well as non-neuronal cells. Assembly MAPs are responsible for cross-linking microtubules in the cytosol. These MAPs are organized into two domains: a basic microtubule-binding domain and an acidic projection domain. The projection domain is the binding site for membranes, intermediate filaments, or other microtubules. Based on sequence analysis, assembly MAPs can be further grouped into two types: Type I and Type II.

Type I MAPs, which include MAP1A and MAP1B, are large, filamentous molecules that co-purify with microtubules and are abundantly expressed in brain and testis. They contain several repeats of a positively-charged amino acid sequence motif that binds and neutralizes negatively charged tubulin, leading to stabilization of microtubules. MAP1A and MAP1B are each derived from a single precursor polypeptide that is subsequently proteolytically processed to generate one heavy chain and one light chain.

Another light chain, LC3, is a 16.4 kDa molecule that binds MAP1A, MAP1B, and microtubules. It is suggested that LC3 is synthesized from a source other than the MAP1A or MAP1B transcripts, and the expression of LC3 may be important in regulating the microtubule binding activity of MAP1A and MAP1B during cell proliferation (Mann, S. S. et al. (1994) J. Biol. Chem. 269:11492–11497).

Type II MAPs, which include MAP2a, MAP2b, MAP2c, MAP4, and Tau, are characterized by three to four copies of an 18-residue sequence in the microtubule-binding domain. MAP2a, MAP2b, and MAP2c are found only in dendrites, MAP4 is found in non-neuronal cells, and Tau is found in axons and dendrites of nerve cells. Alternative splicing of the Tau mRNA leads to the existence of multiple forms of Tau protein. Tau phosphorylation is altered in neurodegenerative disorders such as Alzheimer's disease, Pick's disease, progressive supranuclear palsy, corticobasal degeneration, and familial frontotemporal dementia and Parkinsonism linked to chromosome 17. The altered Tau phosphorylation leads to a collapse of the microtubule network and the formation of intraneuronal Tau aggregates (Spillantini, M. G. and Goedert, M. (1998) Trends Neurosci. 21:428–433).

Microtubular aggregates are associated with several disorders. An extraskeletal myxoid chondrosarcoma tumor from human contained parallel arrays of microtubules within the rough endoplasmic reticulum (Suzuki, T. et al. (1988) J. Pathol. 156:51–57). Microtubular aggregates were also found in hepatocytes from chimpanzees infected with hepatitis C virus. Monoclonal antibodies prepared to these aggregates detect a protein called p44 (or microtubular aggregates protein) (Maeda, T. et al. (1989) J. Gen. Virol. 70:1401–1407). A human homolog of p44 is inducible by interferon-$\alpha$ and interferon-$\beta$, but not by interferon-$\gamma$. p44 protein may be a mediator in the antiviral action of interferon (Kitamura, A. et al. (1994) Eur. J. Biochem. 224:877–883).

The discovery of new microtubule-associated proteins and tubulins, and the polynucleotides encoding them, satisfies a need in the art by providing new compositions which are useful in the diagnosis, prevention, and treatment of cell proliferative, autoimmune/inflammatory, vesicle trafficking, neurological, cell motility, reproductive, and muscle disorders, and in the assessment of the effects of exogenous compounds on the expression of nucleic acid and amino acid sequences of microtubule-associated proteins and tubulins.

SUMMARY OF THE INVENTION

The invention features purified polypeptides, microtubule-associated proteins and tubulins, referred to collectively as "MICAPTUB" and individually as "MICAPTUB-1" and "MICAPTUB-2." In one aspect, the invention provides an isolated polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. In one alternative, the invention provides an isolated polypeptide comprising the amino acid sequence of SEQ ID NO:1-2.

The invention further provides an isolated polynucleotide encoding a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. In one alternative, the polynucleotide encodes a polypeptide selected from the group consisting of SEQ ID NO:1-2. In another alternative, the polynucleotide is selected from the group consisting of SEQ ID NO:3-4.

Additionally, the invention provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. In one alternative, the invention provides a cell transformed with the recombinant polynucleotide. In another alternative, the invention provides a transgenic organism comprising the recombinant polynucleotide.

The invention also provides a method for producing a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2.

The invention further provides an isolated polynucleotide selected from the group consisting of a) a polynucleotide comprising a polynucleotide sequence selected from the group consisting of SEQ ID NO:3-4, b) a polynucleotide comprising a naturally occurring polynucleotide sequence at least 90% identical to a polynucleotide sequence selected from the group consisting of SEQ ID NO:3-4, c) a polynucleotide complementary to the polynucleotide of a), d) a polynucleotide complementary to the polynucleotide of b), and e) an RNA equivalent of a)-d). In one alternative, the polynucleotide comprises at least 60 contiguous nucleotides.

Additionally, the invention provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:3-4, b) a polynucleotide comprising a naturally occurring polynucleotide sequence at least 90% identical to a polynucleotide sequence selected from the group consisting of SEQ ID NO:3-4, c) a polynucleotide complementary to the polynucleotide of a), d) a polynucleotide complementary to the polynucleotide of b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:3-4, b) a polynucleotide comprising a naturally occurring polynucleotide sequence at least 90% identical to a polynucleotide sequence selected from the group consisting of SEQ ID NO:3-4, c) a polynucleotide complementary to the polynucleotide of a), d) a polynucleotide complementary to the polynucleotide of b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2, and a pharmaceutically acceptable excipient. In one embodiment, the composition comprises an amino acid sequence selected from the group consisting of SEQ ID NO:1-2. The invention additionally provides a method of treating a disease or condition associated with decreased expression of functional MICAPTUB, comprising administering to a patient in need of such treatment the composition.

The invention also provides a method for screening a compound for effectiveness as an agonist of a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional MICAPTUB, comprising administering to a patient in need of such treatment the composition.

Additionally, the invention provides a method for screening a compound for effectiveness as an antagonist of a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional MICAPTUB, comprising administering to a patient in need of such treatment the composition.

The invention further provides a method of screening for a compound that specifically binds to a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide selected from the group consisting of a) a polypeptide comprising an amino acid sequence selected from the group consisting of SEQ ID NO:1-2, b) a polypeptide comprising a naturally occurring amino acid sequence at least 90% identical to an amino acid sequence selected from the group consisting of SEQ ID NO:1-2, c) a biologically active fragment of a polypeptide having an amino acid sequence selected from the group consisting of SEQ ID NO:1-2, and d) an immunogenic fragment of a polypeptide having an amino acid sequence selected from the group consisting of SEQ ID NO:1-2. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a polynucleotide sequence selected from the group consisting of SEQ ID NO:3-4, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:3-4, ii) a polynucleotide comprising a naturally occurring polynucleotide sequence at least 90% identical to a polynucleotide sequence selected from the group consisting of SEQ ID NO:3-4, iii) a polynucleotide having a sequence complementary to i), iv) a polynucleotide complementary to the polynucleotide of ii), and v) an RNA equivalent of i)-iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:3-4, ii) a polynucleotide comprising a naturally occurring polynucleotide sequence at least 90% identical to a polynucleotide sequence selected from the group consisting of SEQ ID NO:3-4, iii) a polynucleotide complementary to the polynucleotide of i), iv) a polynucleotide complementary to the polynucleotide of ii), and v) an RNA equivalent of i)-iv). Alternatively, the target polynucleotide comprises a fragment of a polynucleotide sequence selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability score for the match between each polypeptide and its GenBank homolog is also shown.

Table 3 shows structural features of polypeptide sequences of the invention, including predicted motifs and domains, along with the methods, algorithms, and searchable databases used for analysis of the polypeptides.

Table 4 lists the cDNA and/or genomic DNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"MICAPTUB" refers to the amino acid sequences of substantially purified MICAPTUB obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of MICAPTUB. Agonists may include proteins, nucleic acids, carbohydrates, small molecules, or any other compound or composition which modulates the activity of MICAPTUB either by directly interacting with MICAPTUB or by acting on components of the biological pathway in which MICAPTUB participates.

An "allelic variant" is an alternative form of the gene encoding MICAPTUB. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding MICAPTUB include those sequences with deletions, insertions, or substitutions of different nucleotides, resulting in a polypeptide the same as MICAPTUB or a polypeptide with at least one functional characteristic of MICAPTUB. Included within this definition are polymorphisms which may or may not be readily detectable using a particular oligonucleotide probe of the polynucleotide encoding MICAPTUB, and improper or unexpected hybridization to allelic variants, with a locus other than the normal chromosomal locus for the polynucleotide sequence encoding MICAPTUB. The encoded protein may also be "altered," and may contain deletions, insertions, or substitutions of amino acid residues which produce a silent change and result in a functionally equivalent MICAPTUB. Deliberate amino acid substitutions may be made on the basis of similarity in polarity, charge, solubility, hydrophobicity, hydrophilicity, and/or the amphipathic nature of the residues, as long as the biological or immunological activity of MICAPTUB is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of MICAPTUB. Antagonists may include proteins such as antibodies, nucleic acids, carbohydrates, small molecules, or any other compound or composition which modulates the activity of MICAPTUB either by directly interacting with MICAPTUB or by acting on components of the biological pathway in which MICAPTUB participates.

The term "antibody" refers to intact immunoglobulin molecules as well as to fragments thereof, such as Fab, $F(ab')_2$, and Fv fragments, which are capable of binding an epitopic determinant. Antibodies that bind MICAPTUB polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic MICAPTUB, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding MICAPTUB or fragments of MICAPTUB may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of MICAPTUB or the polynucleotide encoding MICAPTUB which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:3-4 comprises a region of unique polynucleotide sequence that specifically identifies SEQ ID NO:3-4, for example, as distinct from any other sequence in the genome from which the fragment was obtained. A fragment of SEQ ID NO:3-4 is useful, for example, in hybridization and amplification technologies and in analogous methods that distinguish SEQ ID NO:3-4 from related polynucleotide sequences. The precise length of a fragment of SEQ ID NO:3-4 and the region of SEQ ID NO:3-4 to which the fragment corresponds are routinely determinable by one of ordinary skill in the art based on the intended purpose for the fragment.

A fragment of SEQ ID NO:1-2 is encoded by a fragment of SEQ ID NO:3-4. A fragment of SEQ ID NO:1-2 comprises a region of unique amino acid sequence that specifically identifies SEQ ID NO:1-2. For example, a fragment of SEQ ID NO:1-2 is useful as an immunogenic peptide for the development of antibodies that specifically recognize SEQ ID NO:1-2. The precise length of a fragment of SEQ ID NO:1-2 and the region of SEQ ID NO:1-2 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI)

Basic Local Alignment Search Tool (BLAST) (Altschul, S. F. et al. (1990) J. Mol. Biol. 215:403–410), which is available from several sources, including the NCBI, Bethesda, Md., and on the Internet at http://www.ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off. 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 μg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 µg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of MICAPTUB which is capable of eliciting an immune response when introduced into a living organism, for example, a mamnal. The term "immunogenic fragment" also includes any polypeptide or oligopeptide fragment of MICAPTUB which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of MICAPTUB. For example, modulation may cause an increase or a decrease in protein activity, binding characteristics, or any other biological, functional, or immunological properties of MICAPTUB.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an MICAPTUB may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of MICAPTUB.

"Probe" refers to nucleic acid sequences encoding MICAPTUB, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60,70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual.* $2^{nd}$ ed., vol. 1–3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing MICAPTUB, nucleic acids encoding MICAPTUB, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 07, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 07, 1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

The Invention

The invention is based on the discovery of new human microtubule-associated proteins and tubulins (MICAPTUB), the polynucleotides encoding MICAPTUB, and the use of these compositions for the diagnosis, treatment, or prevention of cell proliferative, autoimmune/ inflammatory, vesicle trafficking, neurological, cell motility, reproductive, and muscle disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are microtubule-associated proteins and tubulins. For example, SEQ ID NO:1 is 74% identical to Torpedo marmorata alpha-tubulin (GenBank ID g313131) as determined by the Basic Local Alignment Search Tool (BLAST). (See Table 2.) The BLAST probability score is 2.3e-188, which indicates the probability of obtaining the observed polypeptide sequence alignment by chance. SEQ ID NO:1 also contains a tubulin/FtsZ family domain as determined by searching for statistically significant matches in the hidden Markov model (HMM)-based PFAM database of conserved protein family domains. (See Table 3.) Data from BLIMPS and MOTIFS analyses provide further corroborative evidence that SEQ ID NO:1 is an alpha tubulin. In an alternative example, SEQ ID NO:2 is 32% identical to rat microtubule-associated protein 1A MAP1A (GenBank ID g205538) as determined by the Basic Local Alignment Search Tool (BLAST). (See Table 2.) The BLAST probability score is 2.8e-57, which indicates the probability of obtaining the observed polypeptide sequence alignment by chance. Data from BLAST analyses of the PRODOM and DOMO databases provide further corroborative evidence that SEQ ID NO:2 is a microbubule-associated protein. The algorithms and parameters for the analysis of SEQ ID NO:1-2 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:3-4 or that distinguish between SEQ ID NO:3-4 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA and/or genomic sequences in column 5 relative to their respective full length sequences.

The identification numbers in Column 5 of Table 4 may refer specifically, for example, to Incyte cDNAs along with their corresponding cDNA libraries. For example, 5294662H1 is the identification number of an Incyte cDNA sequence, and COLENOT02 is the cDNA library from which it is derived. Incyte cDNAs for which cDNA libraries are not indicated were derived from pooled cDNA libraries (e.g., 70789712V1). Alternatively, the identification numbers in column 5 may refer to GenBank cDNAs or ESTs which contributed to the assembly of the full length polynucleotide sequences. In addition, the identification numbers in column 5 may identify sequences derived from the ENSEMBL (The Sanger Centre, Cambridge, UK) database (i e., those sequences including the designation "ENST"). Alternatively, the identification numbers in column 5 may be derived from the NCBI RefSeq Nucleotide Sequence Records Database (i.e., those sequences including the designation "NM" or "NT") or the NCBI RefSeq Protein Sequence Records (i.e., those sequences including the designation "NP"). Alternatively, the identification numbers in column 5 may refer to assemblages of both cDNA and Genscan-predicted exons brought together by an "exon stitching" algorithm. For example, FL_XXXXXX_$N_1$_ $N_2$_YYYYY_$N_3$_$N_4$ represents a "stitched" sequence in which XXXXXX is the identification number of the cluster of sequences to which the algorithm was applied, and YYYYY is the number of the prediction generated by the algorithm, and $N_{1,2,3}$..., if present, represent specific exons that may have been manually edited during analysis (See Example V). Alternatively, the identification numbers in column 5 may refer to assemblages of exons brought together by an "exon-stretching" algorithm. For example, FLXXXXXX_gAAAAA_gBBBBB_1_N is the identification number of a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
| --- | --- |
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses MICAPTUB variants. A preferred MICAPTUB variant is one which has at least about 80%, or alternatively at least about 90%, or even at least about 95% amino acid sequence identity to the MICAPTUB amino acid sequence, and which contains at least one functional or structural characteristic of MICAPTUB.

The invention also encompasses polynucleotides which encode MICAPTUB. In a particular embodiment, the invention encompasses a polynucleotide sequence comprising a sequence selected from the group consisting of SEQ ID NO:3-4, which encodes MICAPTUB. The polynucleotide sequences of SEQ ID NO:3-4, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding MICAPTUB. In particular, such a variant polynucleotide sequence will have at least about 70%, or alternatively at least about 85%, or even at least about 95% polynucleotide sequence identity to the polynucleotide sequence encoding MICAPTUB. A particular aspect of the invention encompasses a variant of a polynucleotide sequence comprising a sequence selected from the group consisting of SEQ ID NO:3-4 which has at least about 70%, or alternatively at least about 85%, or even at least about 95% polynucleotide sequence identity to a nucleic acid sequence selected from the group consisting of SEQ ID NO:3-4. Any one of the polynucleotide variants described above can encode an amino acid sequence which contains at least one functional or structural characteristic of MICAPTUB.

It will be appreciated by those skilled in the art that as a result of the degeneracy of the genetic code, a multitude of polynucleotide sequences encoding MICAPTUB, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring MICAPTUB, and all such variations are to be considered as being specifically disclosed.

Although nucleotide sequences which encode MICAPTUB and its variants are generally capable of hybridizing to the nucleotide sequence of the naturally occurring MICAPTUB under appropriately selected conditions of stringency, it may be advantageous to produce nucleotide sequences encoding MICAPTUB or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MICAPTUB and its derivatives without altering the encoded amino acid sequences include the production of RNA transcripts having more desirable properties, such as a greater half-life, than transcripts produced from the naturally occurring sequence.

The invention also encompasses production of DNA sequences which encode MICAPTUB and MICAPTUB derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding MICAPTUB or any fragment thereof.

Also encompassed by the invention are polynucleotide sequences that are capable of hybridizing to the claimed polynucleotide sequences, and, in particular, to those shown in SEQ ID NO:3-4 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding MICAPTUB may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode MICAPTUB may be cloned in recombinant DNA molecules that direct expression of MICAPTUB, or fragments or functional equivalents thereof, in appropriate host cells. Due to the inherent degeneracy of the genetic code, other DNA sequences which encode substantially the same or a functionally equivalent amino acid sequence may be produced and used to express MICAPTUB.

The nucleotide sequences of the present invention can be engineered using methods generally known in the art in order to alter MICAPTUB-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C.-C. et al. (1999) Nat. Biotechnol. 17:259–264; and Crameri, A. et al. (1996) Nat. Biotechnol. 14:315–319) to alter or improve the biological properties of MICAPTUB, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding MICAPTUB may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.) Alternatively, MICAPTUB itself or a fragment thereof may be synthesized using chemical methods. For example, peptide synthesis can be performed using various solution-phase or solid-phase techniques. (See, e.g., Creighton, T. (1984) *Proteins, Structures and Molecular Properties*, W H Freeman, New York N.Y., pp. 55–60; and Roberge, J. Y. et al. (1995) Science 269:202–204.) Automated synthesis may be achieved using the ABI 431A peptide synthesizer (Applied Biosystems). Additionally, the amino acid sequence of MICAPTUB, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, supra, pp. 28–53.)

In order to express a biologically active MICAPTUB, the nucleotide sequences encoding MICAPTUB or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding MICAPTUB. Such elements may vary in their strength and specificity. Specific initiation signals may also be used to achieve more efficient translation of sequences encoding MICAPTUB. Such signals include the ATG initiation codon and adjacent sequences, e.g. the Kozak sequence. In cases where sequences encoding MICAPTUB and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding MICAPTUB and appropriate transcriptional and translational control elements. These methods include in vitro recombinant DNA techniques, synthetic techniques, and in vivo genetic recombination. (See, e.g., Sambrook, J. et al. (1989) *Molecular Cloning. A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding MICAPTUB. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Engelhard, E. K. et al. (1994) Proc. Natl. Acad. Sci. USA 91:3224–3227; Sandig, V. et al. (1996) Hum. Gene Ther. 7:1937–1945; Takamatsu, N. (1987) EMBO J. 6:307–311; *The McGraw Hill Yearbook of Science and Technology* (1992) McGraw Hill, New York N.Y., pp. 191–196; Logan, J. and T. Shenk (1984) Proc. Natl. Acad. Sci. USA 81:3655–3659; and Harrington, J. J. et al. (1997) Nat. Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993) Proc. Natl. Acad. Sci. USA 90(13):6340–6344; Buller, R. M. et al. (1985) Nature 317(6040):813–815; McGregor, D. P. et al. (1994) Mol. Immunol. 31(3):219–226; and Verma, I. M. and N. Somia (1997) Nature 389:239–242.) The invention is not limited by the host cell employed.

In bacterial systems, a number of cloning and expression vectors may be selected depending upon the use intended for polynucleotide sequences encoding MICAPTUB. For example, routine cloning, subcloning, and propagation of polynucleotide sequences encoding MICAPTUB can be achieved using a multifunctional E. coli vector such as PBLUESCRIPT (Stratagene, La Jolla Calif.) or PSPORT1 plasmid (Life Technologies). Ligation of sequences encoding MICAPTUB into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of MICAPTUB are needed, e.g. for the production of antibodies, vectors which direct high level expression of MICAPTUB may be used. For example, vectors containing the strong, inducible SP6 or T7 bacteriophage promoter may be used.

Yeast expression systems may be used for production of MICAPTUB. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516–544; and Scorer, C. A. et al. (1994) Bio/Technology 12:181–184.)

Plant systems may also be used for expression of MICAPTUB. Transcription of sequences encoding MICAPTUB may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding MICAPTUB may be ligated into an adenovirus transcription/translation complex consisting of the late promoter and tripartite leader sequence. Insertion in a non-essential E1 or E3 region of the viral genome may be used to obtain infective virus which expresses MICAPTUB in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of MICAPTUB in cell lines is preferred. For example, sequences encoding MICAPTUB can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ and $apr^-$ cells, respectively. (See, e.g., Wigler, M. et al. (1977) Cell 11:223–232; Lowy, L. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding MICAPTUB is inserted within a marker gene sequence, transformed cells containing sequences encoding MICAPTUB can be identified by the absence of marker gene function. Alternatively, a marker gene can be placed in tandem with a sequence encoding MICAPTUB under the control of a single promoter. Expression of the marker gene in response to induction or selection usually indicates expression of the tandem gene as well.

In general, host cells that contain the nucleic acid sequence encoding MICAPTUB and that express MICAPTUB may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of MICAPTUB using either specific polyclonal or monoclonal antibodies are known in the art. Examples of such techniques include enzyme-linked immunosorbent assays (ELISAs), radioimmunoassay (RIAs), and fluorescence activated cell sorting (FACS). A two-site, monoclonal-based immunoassay utilizing monoclonal antibodies reactive to two non-interfering epitopes on MICAPTUB is preferred, but a competitive binding assay may be employed. These and other assays are well known in the art. (See, e.g., Hampton, R. et al. (1990) *Serological Methods a*

*Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding MICAPTUB include oligolabeling, nick translation, end-labeling, or PCR amplification using a labeled nucleotide. Alternatively, the sequences encoding MICAPTUB, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding MICAPTUB may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode MICAPTUB may be designed to contain signal sequences which direct secretion of MICAPTUB through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding MICAPTUB may be ligated to a heterologous sequence resulting in translation of a fusion protein in any of the aforementioned host systems. For example, a chimeric MICAPTUB protein containing a heterologous moiety that can be recognized by a commercially available antibody may facilitate the screening of peptide libraries for inhibitors of MICAPTUB activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the MICAPTUB encoding sequence and the heterologous protein sequence, so that MICAPTUB may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled MICAPTUB may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

MICAPTUB of the present invention or fragments thereof may be used to screen for compounds that specifically bind to MICAPTUB. At least one and up to a plurality of test compounds may be screened for specific binding to MICAPTUB. Examples of test compounds include antibodies, oligonucleotides, proteins (e.g., receptors), or small molecules.

In one embodiment, the compound thus identified is closely related to the natural ligand of MICAPTUB, e.g., a ligand or fragment thereof, a natural substrate, a structural or functional mimetic, or a natural binding partner. (See, e.g., Coligan, J. E. et al. (1991) *Current Protocols in Immunology* 1(2):_Chapter 5.) Similarly, the compound can be closely related to the natural receptor to which MICAPTUB binds, or to at least a fragment of the receptor, e.g., the ligand binding site. In either case, the compound can be rationally designed using known techniques. In one embodiment, screening for these compounds involves producing appropriate cells which express MICAPTUB, either as a secreted protein or on the cell membrane. Preferred cells include cells from mammals, yeast, *Drosophila*, or *E. coli*. Cells expressing MICAPTUB or cell membrane fractions which contain MICAPTUB are then contacted with a test compound and binding, stimulation, or inhibition of activity of either MICAPTUB or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with MICAPTUB, either in solution or affixed to a solid support, and detecting the binding of MICAPTUB to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

MICAPTUB of the present invention or fragments thereof may be used to screen for compounds that modulate the activity of MICAPTUB. Such compounds may include agonists, antagonists, or partial or inverse agonists. In one embodiment, an assay is performed under conditions permissive for MICAPTUB activity, wherein MICAPTUB is combined with at least one test compound, and the activity of MICAPTUB in the presence of a test compound is compared with the activity of MICAPTUB in the absence of the test compound. A change in the activity of MICAPTUB in the presence of the test compound is indicative of a compound that modulates the activity of MICAPTUB. Alternatively, a test compound is combined with an in vitro or cell-free system comprising MICAPTUB under conditions suitable for MICAPTUB activity, and the assay is performed. In either of these assays, a test compound which modulates the activity of MICAPTUB may do so indirectly and need not come in direct contact with the test compound. At least one and up to a plurality of test compounds may be screened.

In another embodiment, polynucleotides encoding MICAPTUB or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999–2002; Wagner, K. U. et al. (1997) Nucleic Acids Res. 25:4323–4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding MICAPTUB may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145–1147).

Polynucleotides encoding MICAPTUB can also be used to create "knockin" humanized animals (pigs) or transgenic animals (mice or rats) to model human disease. With knockin technology, a region of a polynucleotide encoding MICAPTUB is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress MICAPTUB, e.g., by secreting MICAPTUB in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of MICAPTUB and microtubule-associated proteins and tubulins. In addition, the expression of MICAPTUB is closely associated with gastrointestinal tissue and testicular tumor tissue. Therefore, MICAPTUB appears to play a role in cell proliferative, autoimmune/inflammatory, vesicle trafficking, neurological, cell motility, reproductive, and muscle disorders. In the treatment of disorders associated with increased MICAPTUB expression or activity, it is desirable to decrease the expression or activity of MICAPTUB. In the treatment of disorders associated with decreased MICAPTUB expression or activity, it is desirable to increase the expression or activity of MICAPTUB.

Therefore, in one embodiment, MICAPTUB or a fragment or derivative thereof may be administered to a subject to treat or prevent a disorder associated with decreased expression or activity of MICAPTUB. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a vesicle trafficking disorder such as cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminthic, and protozoal infections; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cell motility disorder such as ankylosing spondylitis, Chediak-Higashi syndrome, Duchenne and Becker muscular dystrophy, intrahepatic cholestasis, myocardial hyperplasia, cardiomyopathy, early onset peridontitis, cancers such as adenocarcinoma, ovarian carcinoma, and chronic myelogenous leukemia, and bacterial and helminthic infections; a reproductive disorder such as a disorder of prolactin production, infertility, including tubal disease, ovulatory defects, endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, ectopic pregnancy, teratogenesis; cancer of the breast, fibrocystic breast disease, galactorrhea; a disruption of spermatogenesis, abnormal sperm physiology, cancer of the testis, cancer of the prostate, benign prostatic hyperplasia, prostatitis, Peyronie's disease, impotence, carcinoma of the male breast, gynecomastia, hypergonadotropic and hypogonadotropic hypogonadism, pseudohermaphroditism, azoospermia, premature ovarian failure, acrosin deficiency, delayed puperty, retrograde ejaculation and anejaculation, haemangioblastomas, cystsphaeochromocytomas, paraganglioma, cystadenomas of the epididymis, and endolymphatic sac tumours; and a muscle disorder such as cardiomyopathy, myocarditis, Duchenne's muscular dystrophy, Becker's muscular dystrophy, myotonic dystrophy, central core disease, nemaline myopathy, centronuclear myopathy, lipid myopathy, mitochondrial myopathy, infectious myositis, polymyositis, dermatomyositis, inclusion body myositis, thyrotoxic myopathy, and ethanol myopathy.

In another embodiment, a vector capable of expressing MICAPTUB or a fragment or derivative thereof may be administered to a subject to treat or prevent a disorder associated with decreased expression or activity of MICAPTUB including, but not limited to, those described above.

In a further embodiment, a composition comprising a substantially purified MICAPTUB in conjunction with a suitable pharmaceutical carrier may be administered to a subject to treat or prevent a disorder associated with decreased expression or activity of MICAPTUB including, but not limited to, those provided above.

In still another embodiment, an agonist which modulates the activity of MICAPTUB may be administered to a subject to treat or prevent a disorder associated with decreased expression or activity of MICAPTUB including, but not limited to, those listed above.

In a further embodiment, an antagonist of MICAPTUB may be administered to a subject to treat or prevent a disorder associated with increased expression or activity of MICAPTUB. Examples of such disorders include, but are not limited to, those cell proliferative, autoimmune/inflammatory, vesicle trafficking, neurological, cell motility, reproductive, and muscle disorders described above. In one aspect, an antibody which specifically binds MICAPTUB may be used directly as an antagonist or indirectly as a targeting or delivery mechanism for bringing a pharmaceutical agent to cells or tissues which express MICAPTUB.

In an additional embodiment, a vector expressing the complement of the polynucleotide encoding MICAPTUB may be administered to a subject to treat or prevent a disorder associated with increased expression or activity of MICAPTUB including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MICAPTUB may be produced using methods which are generally known in the art. In particular, purified MICAPTUB may be used to produce antibodies or to screen libraries of pharmaceutical agents to identify those which specifically bind MICAPTUB. Antibodies to MICAPTUB may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with MICAPTUB or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MICAPTUB have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of MICAP- TUB amino acids may be fused with those of another protein, such as KLH, and antibodies to the chimeric molecule may be produced.

Monoclonal antibodies to MICAPTUB may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce MICAPTUB-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for MICAPTUB may also be generated. For example, such fragments include, but are not limited to, F(ab')$_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MICAPTUB and its specific antibody. A two-site, monoclonal-based immunoassay utilizing monoclonal antibodies reactive to two non-interfering MICAPTUB epitopes is generally used, but a competitive binding assay may also be employed (Pound, supra).

Various methods such as Scatchard analysis in conjunction with radioimmunoassay techniques may be used to assess the affinity of antibodies for MICAPTUB. Affinity is expressed as an association constant, $K_a$, which is defined as the molar concentration of MICAPTUB-antibody complex divided by the molar concentrations of free antigen and free antibody under equilibrium conditions. The $K_a$ determined for a preparation of polyclonal antibodies, which are heterogeneous in their affinities for multiple MICAPTUB epitopes, represents the average affinity, or avidity, of the antibodies for MICAPTUB. The $K_a$ determined for a preparation of monoclonal antibodies, which are monospecific for a particular MICAPTUB epitope, represents a true measure of affinity. High-affinity antibody preparations with $K_a$ ranging from about $10^9$ to $10^{12}$ L/mole are preferred for use in immunoassays in which the MICAPTUB-antibody complex must withstand rigorous manipulations. Low-affinity antibody preparations with $K_a$ ranging from about $10^6$ to $10^7$ L/mole are preferred for use in immunopurification and similar procedures which ultimately require dissociation of MICAPTUB, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of MICAPTUB-antibody complexes. Procedures for evaluating antibody specificity, titer, and avidity, and guidelines for antibody quality and usage in various applications, are generally available. (See, e.g., Catty, sunra, and Coligan et al. supra.)

In another embodiment of the invention, the polynucleotides encoding MICAPTUB, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding MICAPTUB. Such technology is well known in the art, and antisense oligonucleotides or larger fragments can be designed from various locations along the coding or control regions of sequences encoding MICAPTUB. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469–475; and Scanlon, K. J. et al. (1995) 9(13):1288–1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J. Pharm. Sci. 87(11):1308–1315; and Morris, M. C. et al. (1997) Nucleic Acids Res. 25(14):2730–2736.)

In another embodiment of the invention, polynucleotides encoding MICAPTUB may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475–480; Bordignon, C. et al. (1995) Science 270:470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404–410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HfV) (Baltimore, D. (1988) Nature 335:395–396; Poeschla, E. et al. (1996) Proc. Natl. Acad. Sci. USA. 93:11395–11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in MICAPTUB expression or regulation causes disease, the expression of MICAPTUB from an appropriate population of transduced cells may alleviate the clinical manifestations caused by the genetic deficiency.

In a further embodiment of the invention, diseases or disorders caused by deficiencies in MICAPTUB are treated by constructing mammalian expression vectors encoding MICAPTUB and introducing these vectors by mechanical means into MICAPTUB-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191–217; Ivics, Z. (1997) Cell 91:501–510; Boulay, J-L. and H. Récipon (1998) Curr. Opin. Biotechnol. 9:445–450).

Expression vectors that may be effective for the expression of MICAPTUB include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). MICAPTUB may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding MICAPTUB from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456–467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to MICAPTUB expression are treated by constructing a retrovirus vector consisting of (i) the polynucleotide encoding MICAPTUB under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A. et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey, R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol. 71:4707–4716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding MICAPTUB to cells which have one or more genetic abnormalities with respect to the expression of MICAPTUB. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544 and Verma, I. M. and N. Somia (1997) Nature 18:389:239–242, both incorporated by reference herein.

In another alternative, a herpes-based, gene therapy delivery system is used to deliver polynucleotides encoding MICAPTUB to target cells which have one or more genetic abnormalities with respect to the expression of MICAPTUB. The use of herpes simplex virus (HSV)-based vectors may be especially valuable for introducing MICAPTUB to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163:152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding MICAPTUB to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for MICAPTUB into the alphavirus genome in place of the capsid-coding region results in the production of a large number of MICAPTUB-coding RNAs and the synthesis of high levels of MICAPTUB in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74–83). The wide host range of alphaviruses will allow the introduction of MICAPTUB into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding MICAPTUB.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MICAPTUB. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding MICAPTUB. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased MICAPTUB expression or activity, a compound which specifically inhibits expression of the polynucleotide encoding MICAPTUB may be therapeutically useful, and in the treatment of disorders associated with decreased MICAPTUB expression or activity, a compound which specifically promotes expression of the polynucleotide encoding MICAPTUB may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding MICAPTUB is exposed to at least one test compound thus obtained. The sample may comprise, for example, an intact or permeabilized cell, or an in vitro cell-free or reconstituted biochemical system. Alterations in the expression of a polynucleotide encoding MICAPTUB are assayed by any method commonly known in the art. Typically, the expression of a specific nucleotide is detected by hybridization with a probe having a nucleotide sequence complementary to the sequence of the polynucleotide encoding MICAPTUB. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of MICAPTUB, antibodies to MICAPTUB, and mimetics, agonists, antagonists, or inhibitors of MICAPTUB.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising MICAPTUB or fragments thereof. For example, liposome preparations containing a cell-impermeable macromolecule may promote cell fusion and intracellular delivery of the macromolecule. Alternatively, MICAPTUB or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example MICAPTUB or fragments thereof, antibodies of MICAPTUB, and agonists, antagonists or inhibitors of MICAPTUB, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MICAPTUB may be used for the diagnosis of disorders characterized by expression of MICAPTUB, or in assays to monitor patients being treated with MICAPTUB or agonists, antagonists, or inhibitors of MICAPTUB. Antibodies useful for diagnostic purposes may be prepared in the same manner as described above for therapeutics. Diagnostic assays for MICAPTUB include methods which utilize the antibody and a label to detect MICAPTUB in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols-for measuring MICAPTUB, including ELISAs, RIAs, and FACS, are known in the art and provide a basis for diagnosing altered or abnormal levels of MICAPTUB expression. Normal or standard values for MICAPTUB expression are established by combining body fluids or cell extracts taken from normal mammalian subjects, for example, human subjects, with antibodies to MICAPTUB under conditions suitable for complex formation. The amount of standard complex formation may be quantitated by various methods, such as photometric means. Quantities of MICAPTUB expressed in subject, control, and disease samples from biopsied tissues are compared with the standard values. Deviation between standard and subject values establishes the parameters for diagnosing disease.

In another embodiment of the invention, the polynucleotides encoding MICAPTUB may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of MICAPTUB may be correlated with disease. The diagnostic assay may be used to determine absence, presence, and excess expression of MICAPTUB, and to monitor regulation of MICAPTUB levels during therapeutic intervention.

In one aspect, hybridization with PCR probes which are capable of detecting polynucleotide sequences, including genomic sequences, encoding MICAPTUB or closely related molecules may be used to identify nucleic acid sequences which encode MICAPTUB. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding MICAPTUB, allelic variants, or related sequences.

Probes may also be used for the detection of related sequences, and may have at least 50% sequence identity to any of the MICAPTUB encoding sequences. The hybridization probes of the subject invention may be DNA or RNA and may be derived from the sequence of SEQ ID NO:3-4 or from genomic sequences including promoters, enhancers, and introns of the MICAPTUB gene.

Means for producing specific hybridization probes for DNAs encoding MICAPTUB include the cloning of polynucleotide sequences encoding MICAPTUB or MICAPTUB derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding MICAPTUB may be used for the diagnosis of disorders associated with expression of MICAPTUB. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a vesicle trafficking disorder such as cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminthic, and protozoal infections; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cell motility disorder such as ankylosing spondylitis, Chediak-Higashi syndrome, Duchenne and Becker muscular dystrophy, intrahepatic cholestasis, myocardial hyperplasia, cardiomyopathy, early onset peridontitis, cancers such as adenocarcinoma, ovarian carcinoma, and chronic myelogenous leukemia, and bacterial and helminthic infections; a reproductive disorder such as a disorder of prolactin production, infertility, including tubal disease, ovulatory defects, endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, ectopic pregnancy, teratogenesis; cancer of the breast, fibrocystic breast disease, galactorrhea; a disruption of spermatogenesis, abnormal sperm physiology, cancer of the testis, cancer of the prostate, benign prostatic hyperplasia, prostatitis, Peyronie's disease, impotence, carcinoma of the male breast, gynecomastia, hypergonadotropic and hypogonadotropic hypogonadism, pseudohermaphroditism, azoospermia, premature ovarian failure, acrosin deficiency, delayed puperty, retrograde ejaculation and anejaculation, haemangioblastomas, cystsphaeochromocytomas, paraganglioma, cystadenomas of the epididymis, and endolymphatic sac tumours; and a muscle disorder such as cardiomyopathy, myocarditis, Duchenne's muscular dystrophy, Becker's muscular dystrophy, myotonic dystrophy, central core disease, nemaline myopathy, centronuclear myopathy, lipid myopathy, mitochondrial myopathy, infectious myositis, polymyositis, dermatomyositis, inclusion body myositis, thyrotoxic myopathy, and ethanol myopathy. The polynucleotide sequences encoding MICAPTUB may be used in Southern or northern analysis, dot blot, or other membrane-based technologies; in PCR technologies; in dipstick, pin, and multiformat ELISA-like assays; and in microarrays utilizing fluids or tissues from patients to detect altered MICAPTUB expression. Such qualitative or quantitative methods are well known in the art.

In a particular aspect, the nucleotide sequences encoding MICAPTUB may be useful in assays that detect the presence of associated disorders, particularly those mentioned above. The nucleotide sequences encoding MICAPTUB may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding MICAPTUB in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of MICAPTUB, a normal or standard profile for expression is established. This may be accomplished by combining body fluids or cell extracts taken from normal subjects, either animal or human, with a sequence, or a fragment thereof, encoding MICAPTUB, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MICAPTUB may involve the use of PCR. These oligomers may be chemically synthesized, generated enzymatically, or produced in vitro. Oligomers will preferably contain a fragment of a polynucleotide encoding MICAPTUB, or a fragment of a polynucleotide complementary to the polynucleotide encoding MICAPTUB, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding MICAPTUB may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding MICAPTUB are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of MICAPTUB include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, MICAPTUB, fragments of MICAPTUB, or antibodies specific for MICAPTUB may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467–471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00–02 from the National Institute of Environmental Health Sciences, released Feb. 29, 2000, available at http://www.niehs.nih.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of,at least 5 contiguous amino acid residues, to the polypeptide sequences of the present invention. In some cases, further sequence data may be obtained for definitive protein identification.

A proteomic profile may also be generated using antibodies specific for MICAPTUB to quantify the levels of MICAPTUB expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding MICAPTUB may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353–7357.)

Fluorescent in situ hybridization (FISH) may be correlated with other physical and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding MICAPTUB on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, MICAPTUB, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between MICAPTUB and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with MICAPTUB, or fragments thereof, and washed. Bound MICAPTUB is then detected by methods well known in the art. Purified MICAPTUB can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MICAPTUB specifically compete with a test compound for binding MICAPTUB. In this manner, antibodies can be used to detect the presence of any peptide which shares one or more antigenic determinants with MICAPTUB.

In additional embodiments, the nucleotide sequences which encode MICAPTUB may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications, and publications mentioned above and below, including U.S. Ser. No. 60/236,015 and U.S. Ser. No. 60/226,797, are hereby expressly incorporated by reference.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), PCR2-TOPOTA (Invitrogen), or pINCY (Incyte Genomics, Palo Alto Calif.), or derivatives thereof. Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361–365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding full length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:3-4. Fragments from about 20 to about 4000 nucleotides which are useful in hybridization and amplification technologies are described in Table 4, column 4.

IV. Identification and Editing of Coding Sequences from Genomic DNA

Putative microtubule-associated proteins and tubulins were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78–94, and Burge, C. and S. Karlin (1998) Curr. Opin. Struct. Biol. 8:346–354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode microtubule-associated proteins and tubulins, the encoded polypeptides were analyzed by querying against PFAM models for microtubule-associated proteins and tubulins. Potential microtubule-associated proteins and tubulins were also identified by homology to Incyte cDNA sequences that had been annotated as microtubule-associated proteins and tubulins. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of MICAPTUB Encoding Polynucleotides

The sequences which were used to assemble SEQ ID NO:3-4 were compared with sequences from the Incyte LIFESEQ database and public domain databases using BLAST and other implementations of the Smith-Waterman algorithm. Sequences from these databases that matched SEQ ID NO:3-4 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Genethon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http://www.ncbi.nlm.nih.gov/genemap/), can be employed to determine if previously identified disease genes map within or in proximity to the intervals indicated above.

In this manner, SEQ ID NO:3 was mapped to chromosome 12 within the interval from 62.7 to 67.3 centiMorgans, and to chromosome 15 within the interval from 32.2 to 45.5 centiMorgans. More than one map location is reported for SEQ ID NO:3, indicating that sequences having different map locations were assembled into a single cluster. This situation occurs, for example, when sequences having strong similarity, but not complete identity, are assembled into a single cluster.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length}(Seq.\ 1), \text{length}(Seq.\ 2)\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and –4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding MICAPTUB are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories.

Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding MICAPTUB. cDNA sequences and cDNA library/tissue information are found in the LIFESEQ GOLD database (Incyte Genomics, Palo Alto Calif.).

VIII. Extension of MICAPTUB Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1×TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:3-4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467–470; Shalon, D. et al. (1996) Genome Res. 6:639–645; Marshall, A. and J. Hodgson (1998) Nat. Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly(A)$^+$ RNA sample is reverse transcribed using MMLV reverse-transcriptase, 0.05 pg/$\mu$l oligo-(dT) primer (21 mer), 1× first strand buffer, 0.03 units/$\mu$l RNase inhibitor, 500 $\mu$M dATP, 500 $\mu$M dGTP, 500 $\mu$M dTTP, 40 $\mu$M dCTP, 40 $\mu$M dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 $\mu$l 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1–2 ng to a final quantity greater than 5 $\mu$g. Amplified array elements are then purified using SEPHACRYL-400 (Amersham Pharmacia Biotech).

Purified array elements are immobilized on polymer-coated glass slides. Glass microscope slides (Coming) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 $\mu$l of the array element DNA, at an average concentration of 100 ng/$\mu$l, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 $\mu$l of sample mixture consisting of 0.2 $\mu$g each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 $\mu$l of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the MICAPTUB-encoding sequences, or any parts thereof, are used to detect, decrease, or inhibit expression of naturally occurring MICAPTUB. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of MICAPTUB. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MICAPTUB-encoding transcript.

XII. Expression of MICAPTUB

Expression and purification of MICAPTUB is achieved using bacterial or virus-based expression systems. For expression of MICAPTUB in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express MICAPTUB upon induction with isopropyl beta-D-thiogalactopyranoside (IPTG). Expression of MICAPTUB in eukaryotic cells is achieved by infecting insect or mammalian cell lines with recombinant Autographica californica nuclear polyhedrosis virus (AcMNPV), commonly known as baculovirus. The nonessential polyhedrin gene of baculovirus is replaced with cDNA encoding MICAPTUB by either homologous recombination or bacterial-mediated transposition involving transfer plasmid intermediates. Viral infectivity is maintained and the strong polyhedrin promoter drives high levels of cDNA transcription. Recombinant baculovirus is used to infect Spodoptera frugiperda (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, MICAPTUB is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from MICAPTUB at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, sura, ch. 10 and 16). Purified MICAPTUB obtained by these methods can be used directly in the assays shown in Examples XVI and XVII where applicable.

XIII. Functional Assays

MICAPTUB function is assessed by expressing the sequences encoding MICAPTUB at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5–10 $\mu$g of recombinant vector are transiently transfected into a human cell line, for example, an endothelial or hematopoietic cell line, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of MICAPTUB on gene expression can be assessed using highly purified populations of cells transfected with sequences encoding MICAPTUB and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding MICAPTUB and other genes of interest can be analyzed by northern analysis or microarray techniques.

XIV. Production of MICAPTUB Specific Antibodies

MICAPTUB substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the MICAPTUB amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-MICAPTUB activity by, for example, binding the peptide or MICAPTUB to a substrate, blocking with 1% BSA, reacting with rabbit antisera, washing, and reacting with radio-iodinated goat anti-rabbit IgG.

XV. Purification of Naturally Occurring MICAPTUB Using Specific Antibodies

Naturally occurring or recombinant MICAPTUB is substantially purified by immunoaffinity chromatography using antibodies specific for MICAPTUB. An immunoaffinity column is constructed by covalently coupling anti-MICAPTUB antibody to an activated chromatographic resin, such as CNBr-activated SEPHAROSE (Amersham Pharmacia Biotech). After the coupling, the resin is blocked and washed according to the manufacturer's instructions.

Media containing MICAPTUB are passed over the immunoaffinity column, and the column is washed under conditions that allow the preferential absorbance of MICAPTUB (e.g., high ionic strength buffers in the presence of detergent). The column is eluted under conditions that disrupt antibody/MICAPTUB binding (e.g., a buffer of pH 2 to pH 3, or a high concentration of a chaotrope, such as urea or thiocyanate ion), and MICAPTUB is collected.

XVI. Identification of Molecules which Interact with MICAPTUB

MICAPTUB, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled MICAPTUB, washed, and any wells with labeled MICAPTUB complex are assayed. Data obtained using different concentrations of MICAPTUB are used to calculate values for the number, affinity, and association of MICAPTUB with the candidate molecules.

Alternatively, molecules interacting with MICAPTUB are analyzed using the yeast two-hybrid system as described in Fields, S. and O. Song (1989) Nature 340:245–246, or using commercially available kits based on the two-hybrid system, such as the MATCHMAKER system (Clontech).

MICAPTUB may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of MICAPTUB Activity

MICAPTUB polymerization is monitored turbidimetrically at 350 nm, 37° C., with a 0.4-cm path thermostated cell in a spectrophotometer. Experiments are performed in a range of concentrations in which the turbidity change is linearly correlated with the amount of sedimented microtubules. Microtubule elongation assays are performed using a preassembled microtubule seed solution (30 μM tubulin) that was 10-fold diluted into the cuvette containing prewarmed MICAPTUB at a series of concentrations in PEM buffer. All pipettings are done gently using truncated warm pipette tips to avoid microtubule breakage (Leguy, R. et al. (2000) J. Biol. Chem. 275:21975–21980).

Alternatively, MICAPTUB activity is measured as GTPase activity, as described by Leguy et al., supra. Briefly, tubulin is incubated with $\alpha^{32}$P-GTP in PEM buffer adjusted to pH6.5 with KOH (80 mM PIPES, 1 mM EGTA, 4 mM Mg +2) containing 5 mM AMP-PNP to inhibit non-specific ATPase activity). MICAPTUB-$\alpha^{32}$P-GTP complexes are separated from free GTP by Sephadex G-25 gel filtration (PD10, Amersham Pharmacia Biotech) and incubated at 37° C. Reactions are acid quenched and processed for Pi extraction.

MICAPTUBs are assayed by their ability to bind to microtubules using a taxol-dependent purification of microtubule-associated proteins similar to that described by Vallee, R. B. (1982, J. Cell Biol. 92:435–442). MICAPTUB prepared from in vitro recombinant cDNA expression systems is incubated with taxol-stabilized bovine brain microtubules (commercially available) in a solution containing GTP and cytosolic extract. Binding of MICAPTUB to polymerized microtubules is measured by cosedimentation at 37° C. The bound and free MICAPTUB are determined by Western blotting with the use of antibodies specific for MICAPTUB and tubulin (Vaillant, A. R. et al. (1998) J. Biol. Chem. 273:13973–13981). The binding of MICAPTUB to microtubules is proportional to the MICAPTUB activity.

In the alternative, an assay for MICAPTUB measures the formation of protein filaments in vitro. A solution of MICAPTUB at a concentration greater than the "critical concentration" for polymer assembly is applied to carbon-coated grids. Appropriate nucleation sites may be supplied in the solution. The grids are negative stained with 0.7% (w/v) aqueous uranyl acetate and examined by electron microscopy. The appearance of filaments of approximately 25 nm (microtubules) is a demonstration of protein activity.

In the alternative, MICAPTUTB activity is associated with its ability to form protein-protein complexes and is measured by its ability to regulate growth characteristics of NIH3T3 mouse fibroblast cells. A cDNA encoding MICAPTUB is subcloned into an appropriate eukaryotic expression vector. This vector is transfected into NIH3T3 cells using methods known in the art. Transfected cells are compared with non-transfected cells for the following quantifiable properties: growth in culture to high density, reduced attachment of cells to the substrate, altered cell morphology, and ability to induce tumors when injected into immunodeficient mice. The activity of MICAPTUB is proportional to the extent of increased growth or frequency of altered cell morphology in NIH3T3 cells transfected with MICAPTUB.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Incyte Polypeptide SEQ ID NO: | Incyte Polypeptide ID | Incyte Polynucleotide SEQ ID NO: | Incyte Polynucleotide ID |
|---|---|---|---|---|
| 4052721 | 1 | 4052721CD1 | 3 | 4052721CB1 |
| 1593855 | 2 | 1593855CD1 | 4 | 1593855CB1 |

TABLE 2

| Polypeptide SEQ ID NO: | Incyte Polypeptide ID | GenBank ID NO: | Probability score | GenBank Homolog |
|---|---|---|---|---|
| 1 | 4052721CD1 | g313131 | 2.3e−188 | [*Torpedo marmorata*] alpha-tubulin (Canals, J. M. et al. (1995) Gene 158: 219–223) |
| 2 | 1593855CD1 | g205538 | 2.8e−57 | [*Rattus norvegicus*] microtubule-associated protein 1A MAP1A (Langkopf, A. (1992) J. Biol. Chem. 267: 16561–16566) |
|  |  | g1790880 | 4.20E−52 | [*Homo sapiens*] microtubule-associated protein 1a (Fink, J. K. et al. Human microtubule-associated protein 1a (MAP1A) gene: genomic organization, cDNA sequence, and developmental- and tissue-specific expression Genomics (1996) 35: 577–585) |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 4052721CD1 | 446 | S101 S169 S200 S248 S294 T129 T172 T39 T80 Y179 | N387 N53 | Tubulin/FtsZ family tubulin: M1–E440 | HMMER_PFAM |
|  |  |  |  |  | Tubulin subunits alpha, beta, gamma signature BL00227: M1–G34, F59–G113, E120-K171, P229-I282, K333-P367, T389-V442 | BLIMPS_BLOCKS |
|  |  |  |  |  | TUBULIN SUBUNITS ALPHA, BETA, AND GAMMA DM00062\|S43144\|157-444: L164-V442 DM00062\|P34690\|155-442: L164-V442 DM00062\|P08070\|154-441: L164-A443 DM00062\|S55911\|155-442: L164-V442 | BLAST_DOMO |
|  |  |  |  |  | TUBULIN CHAIN GTPBINDING MICROTUBULES MULTIGENE FAMILY BETA ALPHA BETATUBULIN BETA1 PD000097: M1-E440 | BLAST_PRODOM |
|  |  |  |  |  | Tubulin subunits alpha, beta, gamma signature Tubulin: G149-G155 | MOTIFS |
| 2 | 1593855CD1 | 681 | S198 S256 S259 S264 S344 S354 S375 S380 S399 S408 S422 S513 S519 S528 S532 S546 S592 S668 S94 S95 T128 T134 T305 T406 T465 T475 T533 T73 | N377 N471 | Signal peptide: M1–G37 | SPSCAN |
|  |  |  |  |  | MICROTUBULE ASSOCIATED MAP1 LIGHT CHAIN PHOSPHORYLATION 1A PD013317: T499-F681 | BLAST_PRODOM |
|  |  |  |  |  | MICROTUBULE ASSOCIATED MAP1 LIGHT CHAIN MICROTUBULES REPEAT PHOSPHORYLATION 1A PD014346: L22-Q170, M1-P13 | BLAST_PRODOM |
|  |  |  |  |  | NEURAXIN AND MAP1B PROTEINS REPEATED REGION DM04499\|P34926\|2393–2773: P302-F681 DM04499\|P46821\|2049–2467: T284-E680 DM04499\|P15205\|458–862: T284-E680 | BLAST_DOMO |
|  |  |  |  |  | MICROTUBULE; 1A; MAP1B; 1B DM03993\|P46821\|222–993: L22-K174, M1-E19, P463-V560, K464-A553, E459-G540, P458-R485 | BLAST_DOMO |

TABLE 4

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| 3 | 4052721CB1 | 1788 | 1–534, 990–1062 | 70789712V1 | 1346 | 1788 |
| | | | | 70787824V1 | 934 | 1480 |
| | | | | 5294662H1 (COLENOT02) | 1 | 248 |
| | | | | 70789158V1 | 276 | 974 |
| | | | | 70791644V1 | 962 | 1606 |
| | | | | 70789276V1 | 150 | 874 |
| 4 | 1593855CB1 | 3298 | 3032–3054 | 4464625H1 (HEALDIT01) | 3077 | 3298 |
| | | | | 6457971H1 (COLNDIC01) | 2423 | 3041 |
| | | | | 6810796J1 (SKIRNOR01) | 1200 | 1914 |
| | | | | 8017582J1 (BMARTXE01) | 1939 | 2565 |
| | | | | 7987486H1 (UTRSTUC01) | 1 | 470 |
| | | | | 7647280J1 (UTRSTUE01) | 388 | 1013 |
| | | | | 155929F1 (THP1PLB02) | 2195 | 2606 |
| | | | | 7712889J2 (TESTTUE02) | 553 | 1239 |
| | | | | 1750475T6 (STOMTUT02) | 2638 | 3287 |
| | | | | 7579226H1 (BRAIFEC01) | 1465 | 1976 |

TABLE 5

| Polynucleotide SEQ ID NO: | Incyte Project ID | Representative Library |
|---|---|---|
| 3 | 4052721CB1 | COLNNOT38 |
| 4 | 1593855CB1 | TESTTUE02 |

TABLE 6

| Library | Vector | Library Description |
|---|---|---|
| COLNNOT38 | pINCY | Library was constructed using RNA isolated from colon tissue removed from a Caucasian male fetus, who died from Patau's syndrome (trisomy 13) at 20-weeks' gestation. |
| TESTTUE02 | PCDNA2.1 | This 5' biased random primed library was constructed using RNA isolated from testicular tumor removed from a 31-year-old Caucasian male during unilateral orchiectomy. Pathology indicated embryonal carcinoma forming a largely necrotic mass involving the entire testicle. Rare foci of residual testicle showed intralobular germ cell neoplasia and tumor was identified at the spermatic cord margin. The patient presented with backache. Patient history included tobacco use. Previous surgeries included a needle biopsy of testis. Patient medications included Colace and antacids. |

TABLE 7

| Program | Description | Reference | Parameter Threshold |
|---|---|---|---|
| ABIFACTURA | A program that removes vector sequences and masks ambiguous bases in nucleic acid sequences. | Applied Biosystems, Foster City, CA. | |
| ABI/ PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403–410; Altschul, S. F. et al. (1997) Nucleic Acids Res. 25: 3389–3402. | ESTs: Probability value = 1.0E−8 or less Full Length sequences: Probability value = 1.0E−10 or less |

TABLE 7-continued

| Program | Description | Reference | Parameter Threshold |
|---|---|---|---|
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444–2448; Pearson, W. R. (1990) Methods Enzymol. 183: 63–98; and Smith, T. F. and M. S. Waterman (1981) Adv. Appl. Math. 2: 482–489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565–6572; Henikoff, J. G. and S. Henikoff (1996) Methods Enzymol. 266: 88–105; and Attwood, T. K. et al. (1997) J. Chem. Inf. Comput. Sci. 37: 417–424. | Probability value = 1.0E−3 or less |
| HMMER | An algorithm for searching a query sequence against hidden Markov model (HMM)-based databases of protein family consensus sequences, such as PFAM. | Krogh, A. et al. (1994) J. Mol. Biol. 235: 1501–1531; Sonnhammer, E. L. L. et al. (1988) Nucleic Acids Res. 26: 320–322; Durbin, R. et al. (1998) Our World View, in a Nutshell, Cambridge Univ. Press, pp. 1–350. | PFAM hits: Probability value = 1.0E−3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61–66; Gribskov, M. et al. (1989) Methods Enzymol. 183: 146–159; Bairoch, A. et al. (1997) Nucleic Acids Res. 25: 217–221. | Normalized quality score ≧ GCG-specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T. F. and M. S. Waterman (1981) J. Mol. Biol. 147: 195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195–202. | |
| SPScan | A weight matrix analysis program that scans protein sequences for the presence of secretory signal peptides. | Nielson, H. et al. (1997) Protein Engineering 10: 1–6; Claverie, J. M. and S. Audic (1997) CABIOS 12: 431–439. | Score = 3.5 or greater |
| TMAP | A program that uses weight matrices to delineate transmembrane segments on protein sequences and determine orientation. | Persson, B. and P. Argos (1994) J. Mol. Biol. 237: 182–192; Persson, B. and P. Argos (1996) Protein Sci. 5: 363–371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. for Artificial Intelligence Press, Menlo Park, CA, pp. 175–182. | |
| Motifs | A program that searches amino acid sequences for patterns that matched those defined in Prosite. | Bairoch, A. et al. (1997) Nucleic Acids Res. 25: 217–221; Wisconsin Package Program Manual, version 9, page M51–59, Genetics Computer Group, Madison, WI. | |

What is claimed is:

1. An isolated polynucleotide encoding an amino acid sequence comprising SEQ ID NO: 1.

2. A recombinant polynucleotide comprising a promoter sequence operably linked to the polynucleotide of claim 1.

3. A cell transformed with the recombinant polynucleotide of claim 2.

4. A method of producing the polypeptide of SEQ ID NO: 1, the method comprising:
   a) culturing the cell of claim 3 under conditions suitable for expression of the polypeptide, and
   b) recovering the polypeptide so expressed.

5. An isolated polynucleotide encoding an amino acid sequence comprising SEQ ID NO: 2.

6. A recombinant polynucleotide comprising a promoter sequence operably linked to the polynucleotide of claim 5.

7. A cell transformed with the recombinant polynucleotide of claim 6.

8. A method of producing the polypeptide of SEQ ID NO: 1, the method comprising:
   a) culturing the cell of claim 7 under conditions suitable for expression of the polypeptide, and
   b) recovering the polypeptide so expressed.

9. An isolate polynucleotide comprising the polynucleotide sequence of SEQ ID NO: 3.

10. A recombinant polynucleotide comprising a promoter sequence operably linked to the polynucleotide of claim 9.

11. A cell transformed with the recombinant polynucleotide of claim 10.

12. An isolated polynucleotide comprising the polynucleotide sequence of SEQ ID NO: 4.

13. A recombinant polynucleotide comprising a promoter sequence operably linked to the polynucleotide of claim 12.

14. A cell transformed with the recombinant polynucleotide of claim 13.

15. An isolated polynucleotide selected from the group consisting of:
   a) a polynucleotide complementary to a polynucleotide sequence selected from the group consisting of SEQ ID: 3-4: or
   b) an RNA equivalent of a).

* * * * *

SEQUENCE LISTING

<160> NUMBER OF SEQ ID NOS: 4

<210> SEQ ID NO 1
<211> LENGTH: 446
<212> TYPE: PRT
<213> ORGANISM: Homo sapiens
<220> FEATURE:
<221> NAME/KEY: misc_feature
<223> OTHER INFORMATION: Incyte ID No: 4052721CD1

<400> SEQUENCE: 1

```
Met Arg Glu Cys Leu Ser Ile His Ile Gly Gln Ala Gly Ile Gln
 1               5                  10                  15

Ile Gly Asp Ala Cys Trp Glu Leu Tyr Cys Leu Glu His Gly Ile
                20                  25                  30

Gln Pro Asn Gly Val Val Leu Asp Thr Gln Gln Asp Gln Leu Glu
                35                  40                  45

Asn Ala Lys Met Glu His Thr Asn Ala Ser Phe Asp Thr Phe Phe
                50                  55                  60

Cys Glu Thr Arg Ala Gly Lys His Val Pro Arg Ala Leu Phe Val
                65                  70                  75

Asp Leu Glu Pro Thr Val Ile Asp Gly Ile Arg Thr Gly Gln His
                80                  85                  90

Arg Ser Leu Phe His Pro Glu Gln Leu Leu Ser Gly Lys Glu Asp
                95                 100                 105

Ala Ala Asn Asn Tyr Ala Arg Gly Arg Tyr Ser Val Gly Ser Glu
               110                 115                 120

Val Ile Asp Leu Val Leu Glu Arg Thr Arg Lys Leu Ala Glu Gln
               125                 130                 135

Cys Gly Gly Leu Gln Gly Phe Leu Ile Phe Arg Ser Phe Gly Gly
               140                 145                 150

Gly Thr Gly Ser Gly Phe Thr Ser Leu Leu Met Glu Arg Leu Thr
               155                 160                 165

Gly Glu Tyr Ser Arg Lys Thr Lys Leu Glu Phe Ser Val Tyr Pro
               170                 175                 180

Ala Pro Arg Ile Ser Thr Ala Val Val Glu Pro Tyr Asn Ser Val
               185                 190                 195

Leu Thr Thr His Ser Thr Thr Glu His Thr Asp Cys Thr Phe Met
               200                 205                 210

Val Asp Asn Glu Ala Val Tyr Asp Ile Cys His Arg Lys Leu Gly
               215                 220                 225

Val Glu Cys Pro Ser His Ala Ser Ile Asn Arg Leu Val Val Gln
               230                 235                 240

Val Val Ser Ser Ile Thr Ala Ser Leu Arg Phe Glu Gly Pro Leu
               245                 250                 255

Asn Val Asp Leu Ile Glu Phe Gln Thr Asn Leu Val Pro Tyr Pro
               260                 265                 270

Arg Ile His Phe Pro Met Thr Ala Phe Ala Pro Ile Val Ser Ala
               275                 280                 285

Asp Lys Ala Tyr His Glu Gln Phe Ser Val Ser Asp Ile Thr Thr
               290                 295                 300

Ala Cys Phe Glu Ser Ser Asn Gln Leu Val Lys Cys Asp Pro Arg
               305                 310                 315

Leu Gly Lys Tyr Met Ala Cys Cys Leu Leu Tyr Arg Gly Asp Val
```

-continued

```
                320                 325                 330
Val Pro Lys Glu Val Asn Ala Ile Ala Ala Thr Lys Ser Arg
                335                 340                 345

His Ser Val Gln Phe Val Asp Trp Cys Pro Thr Gly Phe Lys Val
            350                 355                 360

Gly Ile Asn Asn Arg Pro Pro Thr Val Met Pro Gly Gly Asp Leu
            365                 370                 375

Ala Lys Val His Arg Ser Ile Cys Met Leu Ser Asn Thr Thr Ala
            380                 385                 390

Ile Val Glu Ala Trp Ala Arg Leu Asp His Lys Phe Asp Leu Met
            395                 400                 405

Tyr Ala Lys Arg Ala Phe Leu His Trp Tyr Leu Arg Glu Gly Met
            410                 415                 420

Glu Glu Ala Glu Phe Leu Glu Ala Arg Glu Asp Leu Ala Ala Leu
            425                 430                 435

Glu Arg Asp Tyr Glu Glu Val Ala Gln Ser Phe
            440                 445
```

<210> SEQ ID NO 2
<211> LENGTH: 681
<212> TYPE: PRT
<213> ORGANISM: Homo sapiens
<220> FEATURE:
<221> NAME/KEY: misc_feature
<223> OTHER INFORMATION: Incyte ID No: 1593855CD1

<400> SEQUENCE: 2

```
Met Gly Val Gly Arg Leu Asp Met Tyr Val Leu His Pro Pro Ser
 1               5                  10                  15

Ala Gly Ala Glu Arg Thr Leu Ala Ser Val Cys Ala Leu Leu Val
                20                  25                  30

Trp His Pro Ala Gly Pro Gly Glu Lys Val Val Arg Val Leu Phe
            35                  40                  45

Pro Gly Cys Thr Pro Pro Ala Cys Leu Leu Asp Gly Leu Val Arg
        50                  55                  60

Leu Gln His Leu Arg Phe Leu Arg Glu Pro Val Val Thr Pro Gln
    65                  70                  75

Asp Leu Glu Gly Pro Gly Arg Ala Glu Ser Lys Glu Ser Val Gly
                80                  85                  90

Ser Arg Asp Ser Ser Lys Arg Glu Gly Leu Leu Ala Thr His Pro
                95                 100                 105

Arg Pro Gly Gln Glu Arg Pro Gly Val Ala Arg Lys Glu Pro Ala
            110                 115                 120

Arg Ala Glu Ala Pro Arg Lys Thr Glu Lys Glu Ala Lys Thr Pro
            125                 130                 135

Arg Glu Leu Lys Lys Asp Pro Lys Pro Ser Val Ser Arg Thr Gln
            140                 145                 150

Pro Arg Glu Val Arg Arg Ala Ala Ser Ser Val Pro Asn Leu Lys
            155                 160                 165

Lys Thr Asn Ala Gln Ala Ala Pro Lys Pro Arg Lys Ala Pro Ser
            170                 175                 180

Thr Ser His Ser Gly Phe Pro Pro Val Ala Asn Gly Pro Arg Ser
            185                 190                 195

Pro Pro Ser Leu Arg Cys Gly Glu Ala Ser Pro Pro Ser Ala Ala
            200                 205                 210
```

```
Cys Gly Ser Pro Ala Ser Gln Leu Val Ala Thr Pro Ser Leu Glu
            215                 220                 225

Leu Gly Pro Ile Pro Ala Gly Glu Glu Lys Ala Leu Glu Leu Pro
            230                 235                 240

Leu Ala Ala Ser Ser Ile Pro Arg Pro Arg Thr Pro Ser Pro Glu
            245                 250                 255

Ser His Arg Ser Pro Ala Glu Gly Ser Glu Arg Leu Ser Leu Ser
            260                 265                 270

Pro Leu Arg Gly Gly Glu Ala Gly Pro Asp Ala Ser Pro Thr Val
            275                 280                 285

Thr Thr Pro Thr Val Thr Thr Pro Ser Leu Pro Ala Glu Val Gly
            290                 295                 300

Ser Pro His Ser Thr Glu Val Asp Glu Ser Leu Ser Val Ser Phe
            305                 310                 315

Glu Gln Val Leu Pro Pro Ser Ala Pro Thr Ser Glu Ala Gly Leu
            320                 325                 330

Ser Leu Pro Leu Arg Gly Pro Arg Ala Arg Arg Ser Ala Ser Pro
            335                 340                 345

His Asp Val Asp Leu Cys Leu Val Ser Pro Cys Glu Phe Glu His
            350                 355                 360

Arg Lys Ala Val Pro Met Ala Pro Ala Pro Ala Ser Pro Gly Ser
            365                 370                 375

Ser Asn Asp Ser Ser Ala Arg Ser Gln Glu Arg Ala Gly Gly Leu
            380                 385                 390

Gly Ala Glu Glu Thr Pro Pro Thr Ser Val Ser Glu Ser Leu Pro
            395                 400                 405

Thr Leu Ser Asp Ser Asp Pro Val Pro Leu Ala Pro Gly Ala Ala
            410                 415                 420

Asp Ser Asp Glu Asp Thr Glu Gly Phe Gly Val Pro Arg His Asp
            425                 430                 435

Pro Leu Pro Asp Pro Leu Lys Val Pro Pro Pro Leu Pro Asp Pro
            440                 445                 450

Ser Ser Ile Cys Met Val Asp Pro Glu Met Leu Pro Pro Lys Thr
            455                 460                 465

Glu Arg Gln Thr Glu Asn Val Ser Arg Thr Arg Lys Pro Leu Ala
            470                 475                 480

Arg Pro Asn Ser Arg Ala Ala Ala Pro Lys Ala Thr Pro Val Ala
            485                 490                 495

Ala Ala Lys Thr Lys Gly Leu Ala Gly Gly Asp Arg Ala Ser Arg
            500                 505                 510

Pro Leu Ser Ala Arg Ser Glu Pro Ser Glu Lys Gly Gly Arg Ala
            515                 520                 525

Pro Leu Ser Arg Lys Ser Ser Thr Pro Lys Thr Ala Thr Arg Gly
            530                 535                 540

Pro Ser Gly Ser Ala Ser Ser Arg Pro Gly Val Ser Ala Thr Pro
            545                 550                 555

Pro Lys Ser Pro Val Tyr Leu Asp Leu Ala Tyr Leu Pro Ser Gly
            560                 565                 570

Ser Ser Ala His Leu Val Asp Glu Glu Phe Phe Gln Arg Val Arg
            575                 580                 585

Ala Leu Cys Tyr Val Ile Ser Gly Gln Asp Gln Arg Lys Glu Glu
            590                 595                 600

Gly Met Arg Ala Val Leu Asp Ala Leu Leu Ala Ser Lys Gln His
```

```
                605                 610                 615
Trp Asp Arg Asp Leu Gln Val Arg Val Thr Pro Gly Pro Leu Val
            620                 625                 630

Val Thr Leu Ile Pro Thr Phe Asp Ser Val Ala Met His Thr Trp
            635                 640                 645

Tyr Ala Glu Thr His Ala Arg His Gln Ala Leu Gly Ile Thr Val
            650                 655                 660

Leu Gly Ser Asn Ser Met Val Ser Met Gln Asp Asp Ala Phe Pro
            665                 670                 675

Ala Cys Lys Val Glu Phe
            680

<210> SEQ ID NO 3
<211> LENGTH: 1788
<212> TYPE: DNA
<213> ORGANISM: Homo sapiens
<220> FEATURE:
<221> NAME/KEY: misc_feature
<223> OTHER INFORMATION: Incyte ID No: 4052721CB1

<400> SEQUENCE: 3
gggcacgttc tcatcagcat gagggagtgc ctttccatcc acatcggtca agctggcatc      60
cagattgggg acgcctgctg ggaactctat tgcctggaac atggaatcca gccaaatggc     120
gttgttcttg acactcaaca ggatcagctg gaaaatgcaa aaatggagca cacaaatgca     180
tctttcgata ccttcttctg tgagacaaga gctgggaagc atgtgcctag agcactcttc     240
gtggacttgg agccaactgt tatagatggg atccggacgg gccagcaccg ttcactcttc     300 cacccccgagc agctccttag cggaaaggag gatgctgcta acaattacgc gcgaggccgt     360
tactctgtgg ggtcggaggt catcgacctt gtgctggaga ggacccggaa gctggcagaa     420
cagtgtggtg gacttcaggg atttttgatt ttccgaagct tggaggagg cactggttca     480 gggtttacgt ctctcttaat ggagaggctc acaggagaat atagcagaaa gactaagctg     540
gagttctcgg tctacccagc ccccaggatc tccactgctg tggtagagcc ttataactct     600
gtcctcacca cccactccac cacagagcac acggactgta ccttcatggt ggacaacgag     660
gccgtctatg atatatgcca tcgtaaactc ggtgttgaat gccctctca tgccagcatc     720 aatagattgg tggttcaggt ggtatcttcc atcactgcct ccctccggtt tgaagggccc     780
ttgaatgtag acctaattga attccagacc aacctggtac cttatccgag aatacatttc     840
cccatgacag ccttcgcccc catcgtctct gctgacaaag cctaccatga gcagttctct     900
gtgtcagaca tcaccactgc ctgctttgag tcctccaacc agctggtcaa gtgtgatcct     960
cggcttggga agtacatggc ctgctgccta ctctatagag gggatgtggt ccccaaggaa    1020
gtgaatgcag caatcgcagc cacgaagtcg aggcactctg ttcagtttgt agattggtgt    1080
ccaactggtt tcaaggtggg catcaacaat cggccgccca cggtgatgcc gggtggggac    1140
ctggccaaag tccaccggtc catctgcatg ctgagcaaca ccacggcgat tgtggaggcc    1200
tgggcccgcc tggaccacaa gtttgacctc atgtacgcca agagcatt tctgcactgg     1260 tacctcagag aaggcatgga agaagcagag ttcttggagg ccaggaaga tctggcagcc    1320 ctggagaggg actatgagga agtggcgcaa gtttctgag gcatgtatga tgggtgcaaa    1380
tgaatgtcaa gttaaaatgg catgtttttct tttcaagccg ttatatgcct agtgggtagt    1440
tcccctgatg agcagaaaaa tgaactcaaa tcaggcaaga ctctaggttc acactaaat     1500 taagtgggtc agtaccaaca atgaacacat tatttcctgg tctactggta caagtcagct    1560
```

-continued

| | |
|---|---|
| ctgctacctg ggagcctttg gaagcttaga gtcctttgaa ctgctgagtc acttctaggt | 1620 |
| gggattttt tgttttacca agagacaatg aaatcctgaa gtttatgctt ttcctttctg | 1680 |
| gtaccggaag tagaaaacag cacatgttga ttacgaatgt ttttccccc atgtctacat | 1740 |
| ttttacact gattaaatca taaatatttt cagtaaaaaa aaaaaggg | 1788 |

<210> SEQ ID NO 4
<211> LENGTH: 3298
<212> TYPE: DNA
<213> ORGANISM: Homo sapiens
<220> FEATURE:
<221> NAME/KEY: misc_feature
<223> OTHER INFORMATION: Incyte ID No: 1593855CB1

<400> SEQUENCE: 4

| | |
|---|---|
| gggatggcg gcggtggctg gatctggggc tgccgcggct ccgagctcac tgctcctcgt | 60 |
| ggtgggcagc gagttcggga gcccggggct cctcacctac gtcctggagg agctcgaaag | 120 |
| aggcatccgg tcttgggatg tcgatcctgg cgtctgcaac cttgatgaac agctcaaggt | 180 |
| ctttgtgtcc cgacactctg ccaccttctc cagcattgtg aaaggccagc ggagcctgca | 240 |
| ccaccgtgga gacaacctgg agaccctggt cctcctgaac ccatcagaca gtccctgta | 300 |
| tgatgagctc cggaaccttc tgttggaccc tgcctctcac aagctactgg tgttggctgg | 360 |
| gccctgcctg gaggagacgg gggagctgct gctacagaca gggggcttct cgcctcacca | 420 |
| cttcctccag gtcctgaagg acagagagat ccgggacatc ctggccacca cgccccacc | 480 |
| tgtgcagccg cccatactca ccatcacctg ccccaccttc ggtgactggg ctcagctggc | 540 |
| acccgctgtg cctggccttc aggggcgct ccggctccag ctgcggctga accccccggc | 600 |
| gcagctgccc aactctgagg gcctgtgcga attcctggag tacgtggctg agtctctgga | 660 |
| gccaccgtcc cccttcgagc tgctggagcc cccgacctcc gggggcttcc tcaggctggg | 720 |
| ccggccctgc tgctacatct tccctggagg cctcgggat gccgccttct tcgccgtcaa | 780 |
| tggcttcact gtgctggtca acggtggctc aaaccccaag tccagttttct ggaagctggt | 840 |
| gcggcacctg gaccgcgtgg atgccgtgct ggtgaccac cctggcgccg acagcctccc | 900 |
| cggcctcaac agcctgctgc ggcgcaaact ggcggagcgc tccgaggtgg ctgctggtgg | 960 |
| gggctcctgg gacgacaggc tgcgcaggct catctccccc aacctggggg tcgtgttctt | 1020 |
| caacgcctgc gaggccgcgt cgcggctggc gcgcggcgag gatgaggcgg agctggcgct | 1080 |
| gagcctcctg gcgcagctgg gcatcacgcc tctgccactc agccgcggcc ccgtgccagc | 1140 |
| caaacccacc gtgctcttcg agaagatggg cgtgggccgg ctggacatgt atgtgctgca | 1200 |
| cccgccctcc gccggcgccg agcgcacgct ggcctctgtg tgccgccctgc tggtgtggca | 1260 |
| ccccgccggc ccggcgaga aggtggtgcg cgtgctgttc cccggttgca ccccgcccgc | 1320 |
| ctgcctcctg gacggcctgg tccgcctgca gcacttgagg ttcctgcgag agcccgtggt | 1380 |
| gacgccccag gacctggagg ggccggggcg agccgagagc aaagagagcg tgggctcccg | 1440 |
| ggacagctcg aagagagagg gcctcctggc cacccaccct agacctggcc aggagcgccc | 1500 |
| tggggtggcc cgcaaggagc cagcacgggc tgaggcccca cgcaagactg agaaagaagc | 1560 |
| caagaccccc cgggagttga agaaagaccc caaaccgagt gtctcccgga cccagccgcg | 1620 |
| ggaggtgcgc cgggcagcct cttctgtgcc caacctcaag aagacgaatg cccaggcggc | 1680 |
| acccaagccc cgcaaagcgc ccagcacgtc ccactctggc ttcccgccgg tgcaaatgg | 1740 |
| accccgcagc ccgcccagcc tccgatgtgg agaagccagc ccccccagtg cagcctgcgg | 1800 |

```
                                        -continued ctctccggcc tcccagctgg tggccacgcc cagcctggag ctggggccga tcccagccgg    1860
ggaggagaag gcactggagc tgcctttggc cgccagctca atcccaaggc cacgcacacc    1920
ctcccctgag tcccaccgga gccccgcaga gggcagcgag cggctgtcgc tgagcccact    1980
gcggggcggg gaggccgggc cagacgcctc acccacagtg accacaccca cggtgaccac    2040
gccctcacta cccgcagagg tgggctcccc gcactcgacc gaggtggacg agtccctgtc    2100
ggtgtccttt gagcaggtgc tgccgccatc cgcccccacc agtgaggctg ggctgagcct    2160
cccgctgcgt ggcccccggg cgcggcgctc ggcttcccca cacgatgtgg acctgtgcct    2220
ggtgtcaccc tgtgaatttg agcatcgcaa ggcggtgcca atggcaccgg cacctgcgtc    2280
ccccggcagc tcgaatgaca gcagtgcccg gtcacaggaa cgggcaggtg ggctgggggc    2340
cgaggagacg ccacccacat cggtcagcga gtccctgccc accctgtctg actcggatcc    2400 cgtgccctg gccccggtg cggcagactc agacgaagac acagagggct ttggagtccc       2460
tcgccacgac cctttgcctg acccctcaa ggtcccccca ccactgcctg acccatccag       2520
catctgcatg gtggaccccg agatgctgcc ccccaagaca gaacggcaaa cggagaacgt    2580
cagccgcacc cggaagcccc tggcccgccc caactcacgc gctgccgccc ccaaagccac    2640
tccagtggct gctgccaaaa ccaagggggct tgctggtggg gaccgtgcca gccgaccact  2700
cagtgcccgg agtgagccca gtgagaaggg aggccgggca cccctgtcca gaaagtcctc    2760 aaccccaag actgccactc gaggcccgtc ggggtcagcc agcagccggc ccggggtgtc     2820
agccacccca cccaagtccc cggtctacct ggacctggcc tacctgccca gcgggagcag    2880
cgcccacctg gtggatgagg agttcttcca gcgcgtgcgc gcgctctgct acgtcatcag    2940
tggccaggac cagcgcaagg aggaaggcat gcgggccgtc ctggacgcgc tactggccag    3000
caagcagcat tgggaccgtg acctgcaggt gcgtgtcacc ccagggcctc tggtggtgac    3060
cctgatcccc actttcgact cggtggccat gcatacgtgg tacgcagaga cgcacgcccg    3120
gcaccaggcg ctgggcatca cggtgttggg cagcaacagc atggtgtcca tgcaggatga    3180
cgccttcccg gcctgcaagg tggagttcta gccccatcgc cgacacgccc cccactcagc    3240
ccagcccgcc tgtccctaga ttcagccaca tcagaaataa actgtgacta cacttggc     3298
```